(12) United States Patent
Nehls

(10) Patent No.: US 8,114,138 B2
(45) Date of Patent: Feb. 14, 2012

(54) VERTEBRAL TEMPLATE SYSTEMS AND METHODS OF USE

(76) Inventor: Daniel Nehls, Tacoma, WA (US)

( * ) Notice: Subject to any disclaimer, the term of this patent is extended or adjusted under 35 U.S.C. 154(b) by 630 days.

(21) Appl. No.: 12/333,260

(22) Filed: Dec. 11, 2008

(65) Prior Publication Data

US 2010/0152781 A1   Jun. 17, 2010

(51) Int. Cl.
*A61B 17/88* (2006.01)
(52) U.S. Cl. ........ 606/281; 606/102; 606/280; 606/914; 606/915
(58) Field of Classification Search .................. 606/281, 606/282, 915, 86 A, 86 B, 914
See application file for complete search history.

(56) References Cited

U.S. PATENT DOCUMENTS 6,398,783 B1 * 6/2002 Michelson ...................... 606/70
2006/0293670 A1 * 12/2006 Smisson et al. .................. 606/69
* cited by examiner

*Primary Examiner* — Thomas C. Barrett
*Assistant Examiner* — Andrew Yang
(74) *Attorney, Agent, or Firm* — Baumgartner Patent Law; Marc Baumgartner

(57) ABSTRACT

Template systems and methods of use are disclosed herein for use in conjunction with corresponding spinal fusion plates. Preferred templates are slotted to allow for use with distractor pins and a distractor. Additionally preferred templates include windows to allow the operating surgeon to have more visibility of the intervertebral area, including the graft. After the appropriate sized template has been placed against the targeted vertebrae, holding pins can be placed into the vertebral bodies to help guide the fusion plate and to compress the intervertebral space.

11 Claims, 5 Drawing Sheets

VERTEBRAL TEMPLATE SYSTEMS AND METHODS OF USE

FIELD OF THE INVENTION

The embodiments herein relate to template systems and methods useful in bone fixation procedures. More particularly, the teaching herein relate to improving current methods and systems directed to fusing one or more adjacent vertebrae.

BACKGROUND

The spine consists of a series of bone structures termed "vertebrae." Between each vertebra is a flexible, connective tissue termed an "intervertebral disc" which secures one vertebra to another and functions as a shock absorber. Spinal fixation is a surgical technique in which one or more of the vertebrae of the spine are joined by an implant (e.g., a plate or rods.) to prevent relative movement of the spine, with the goal of live bone eventually fusing the adjacent vertebrae together.

Patients requiring spinal fusion typically suffer from either neurological deficits or severe pain which has not responded to conservative treatment. Typical conditions that are treated by spinal fusion procedure non-exclusively include: degenerative spinal conditions, discogenic pain, spinal tumor, vertebral fracture, scoliosis, kyphosis, spondylolisthesis, spondylosis, and other conditions that causes instability or pain in the spine.

Typically a spinal fixation procedure does not connect the patient's original vertebrae directly together; rather the intervertebral disc is usually completely or partially removed (disectomy) and/or one or more entire vertebral bodies are removed (corpectomy). The space remaining from the removed discs and vertebral bodies after a disectomy or corpectomy is typically replaced by a graft positioned between adjacent vertebrae to maintain proper length in the spinal column. After the surgery, it is desired that living bone from the vertebrae spans the inter-body graft thereby fusing the adjacent vertebrae together.

Traditionally, interbody grafts are fashioned from bone taken from a patient's skeleton, and are also referred to as "autografts." As the harvesting of an autograft is painful for the patient, many surgeons now prefer the use of "allografts" which are harvested from a body other than the patient's. Interbody grafts may also be formed from synthetic materials such as titanium, carbon fiber and plastics. Unfortunately, grafts are associated with a relatively high rate of dislodgement due to the patient's neck movement during the healing process. To minimize the risk of dislodgement of the interbody graft posteriorly, toward the spinal cord, surgeons routinely mortise the graft by drilling a shelf into the vertebrae. To minimize the risk of dislodgement of the interbody graft anteriorly, surgeons routinely place a fusion plate across the inner space and secure it with screws extending into the vertebrae.

Placement of an anterior cervical plate with a screw fixation is effective in preventing interbody graft dislodgement toward the esophagus and also enhances fusion by providing rigid fixation between the vertebrae.

Presently, in performing a disectomy or corpectomy, a distractor is used to spread the adjacent vertebrae so that the disc or vertebral body of interest can be removed. In use, a pair of distractor pins having heads for engaging with a distractor are screwed into the vertebrae adjacent to the disectomy or corpectomy site. One pin is placed in the superior vertebra, and a second pin is placed in the inferior vertebra. The distractor is then coupled to the heads of pins on the upper and lower vertebrae, above and below the site, and the vertebrae are then mechanically spread apart, for aiding in the removal of any remaining portion of the deteriorated disc or vertebral body, and also for creating a gap for placing the graft. According to most traditional methods, the distractor and distractor pins are removed after the bone graft is positioned, and before a fusion plate is fixed onto the lower and upper vertebrae.

The above-described method has many disadvantages, one being that it relies on the natural weight of the spine to compress the intervertebral graft between the upper and lower vertebral bodies. Natural compression alone is often insufficient as it can create undesirable space between the vertebral members and thus reduces the likelihood that fusion will occur. U.S. Pat. No. 6,648,891, to Kim (which is hereby expressly incorporated by reference herein in its entirety) attempted to address this issue by describing a system that allows a slotted fusion plate to be screwed into the desired vertebral bodies while the distractor and the distractor pins remain in the vertebrae (See Kim, cols. 2-3). More specifically, these plates include the upper and lower slots configured to be used with distractor pins, and therefore allow a surgeon to utilize a distractor to apply "mechanical compression" on the intervertebral graft as the final fusion plate is secured.

Unfortunately, the fusion plates provided by Kim are not a complete solution. Even though the slotted plates are configured to be used while the distractor pins are still attached to the vertebral bodies, they do not allow for an unobstructed view of the spine, including the intervertebral space where the graft is positioned during the operation. Without an unobstructed view, surgeons are more likely to accidentally position the screw into the graft, which could push it into the patient's spinal cord. It is important to note that adding a central window to the Kim plates would not be an obvious modification. To explain, it is first noted that the screw holes on the plate need to be of a considerable size to accommodate the final screws. This is important because the width of the plate is limited by the width of the vertebral bodies, and thus there is a limited amount of space on the plate for both upper and lower slots and the screw holes. Due to this constraint, the bigger the screw holes are on the plate, the less available space there will be for the slots, and vice versa. This sizing and positioning problem is compounded if the final plate also includes a central window for viewing the graft. Having a large viewing window, screw holes, and distractor pin slots on the final plate can also compromise the strength of the final plate, especially if it is a smaller sized plate.

Thus, there is a need in the art for improved procedures and systems for applying a fusion plate to a patient's spine, following a corpectomy or disectomy, that provide sufficient pressure to the spine and an optimum viewing area for the surgeon to work, without utilizing potentially weakened, or poorly configured plates.

SUMMARY OF THE INVENTION

Preferred embodiments are directed to templates adapted to be removably positioned over superior and inferior vertebral bodies and a first intervertebral space, and having a top section configured to be positioned on the superior vertebral body and comprising a first vertical slot adapted to receive a first distractor pin and that divides the top section into first and second upper corner areas, wherein at least one of the upper corner areas comprise a first holding pin aperture; a bottom section configured to be positioned on the inferior vertebral body and comprising a second vertical slot adapted to receive a second distractor pin and that divides the bottom section into first and second lower corner areas, wherein at least one of the lower corner areas comprises a second holding pin aperture; and a first window positioned between the top and bottom sections and configured to be positioned over the first intervertebral space.

Preferably, the first and second holding pin apertures are vertically aligned with another and the four corner areas each include a holding pin aperture.

According to specific embodiments, the first and second holding pin apertures are variable-size apertures that individually include multiple positions for a holding pin to be placed.

Preferably, the first vertical slot partially bifurcates the top section down the middle of the template and the second vertical slot partially bifurcates the bottom section up the middle of the template.

Alternatively, the templates herein can further include a middle section configured to be positioned against a middle vertebral body in between the superior and inferior vertebral bodies. More specifically, the first window can be positioned between the top and middle sections of the template and can be configured to be positioned over the first intervertebral space between the superior and middle vertebral bodies. The template can further comprise a second window positioned between the bottom and middle sections of the template and can be configured to be positioned over a second intervertebral space between the inferior and middle vertebral bodies.

Further embodiments are directed to methods of using the templates herein to select a fusion plate for implanting onto a superior and inferior vertebral body having a graft implanted between a first intervertebral space comprising: (a) inserting a first distractor pin into the superior vertebral body and a second distractor pin into the inferior vertebrae; (b) engaging said distractor pins with a distractor; (c) compressing the intervertebral space and graft with the distractor; (d) providing a template, (e) placing the template on the compressed superior and inferior vertebrae such that the first vertical slot receives the first distractor pin, the second vertical slot receives the second distractor pin, and the first window is positioned over the first intervertebral space; and (f) selecting a final fusion plate for implantation onto the superior and inferior vertebral bodies that comprises first and second screw holes aligned with the first and second holding pin apertures on the template.

Further methods are directed to using the templates herein for implanting a fusion plate onto a superior and inferior vertebral body having a graft implanted between a first intervertebral space comprising: (a) inserting a first distractor pin into the superior vertebral body and a second distractor pin into the inferior vertebrae; (b) engaging said distractor pins with a distractor; (c) compressing the intervertebral space and graft with the distractor; (d) providing a template, (e) placing the template on the compressed superior and inferior vertebrae such that the first vertical slot receives the first distractor pin, the second vertical slot receives the second distractor pin, and the first window is positioned over the first intervertebral space; (f) selecting a final fusion plate for implantation onto the superior and inferior vertebral bodies that comprises first and second screw holes aligned with the first and second holding pin apertures on the template; (g) placing a first holding pin into the superior vertebral body through the first holding pin aperture; (h) placing a second holding pin into the inferior vertebral body through the second holding pin aperture; (i) removing the template from the superior and inferior vertebral bodies; (j) removing distractor pins from the superior and inferior vertebral bodies; (k) placing the fusion plate onto the superior and inferior vertebral bodies such that the first and second holding pins pass through the first and second aligned screw holes on the fusion plate and compress the first intervertebral space; and (l) securing said fusion plate to the superior and inferior vertebral bodies.

BRIEF DESCRIPTION OF THE DRAWINGS

It will be appreciated that the drawings are not necessarily to scale, with emphasis instead being placed on illustrating the various aspects and features of embodiments of the invention, in which.

DETAILED DESCRIPTION OF THE ILLUSTRATED EMBODIMENTS

Figure 1:
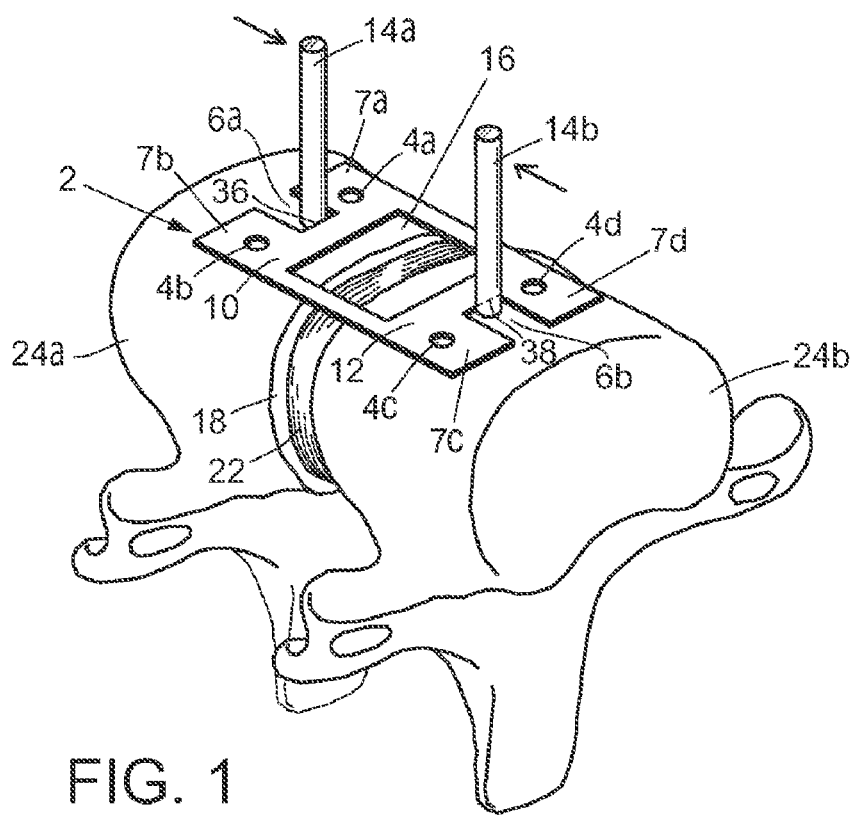
FIG. 1 is a perspective view of a preferred template being positioned on adjacent vertebral bodies.

Embodiments of the present invention are described below with reference to the above described Figures. It is, however, expressly noted that the present invention is not limited to the embodiments depicted in the Figures, but rather the intention is that modifications that are apparent to the person skilled in the art and equivalents thereof are also included.

According to preferred systems and methods, a surgeon first removes the intervertebral disc (disectomy) and/or one or more vertebral bodies (corpectomy), or portions thereof, by using a distractor. In general, distractor pins 14a and 14b are individually fixed to vertebral bodies 24a and 24b respectively, which are positioned superior and inferior to the designated disc or section being removed. Typically, the distractor pins 14a and 14b are screwed into the vertebral bodies 24a and 24b. A distractor tool engages the exposed heads of the pins (14a and 14b) and expands to mechanically separate the vertebral bodies 24a and 24b to allow the surgeon better access to the designated disc or section to be removed.

Distractors and methods of distracting are known in the art and any suitable one can be used with the teachings herein. One non-exclusive example of a distractor/retractor that can be used for separating vertebral bodies is disclosed in U.S. Patent Application No. 2006/0084844, published Apr. 20, 2006 to Daniel G. Nehls, which is hereby expressly incorporated by reference herein in its entirety. After the designated disc material and/or vertebral body is removed, a graft 22 can be inserted into the resulting space, using techniques and materials that are well known in the art. The surgeon then preferably uses the distractor tool which is engaged with the distractor pins 14*a* and 14*b* to compress the intervertebral space 18 and more preferably the graft 22. This compression can allow the graft 22 to have better contact with the vertebral endplates, and thus increase the chances of incorporation.

Preferred methods and systems provided herein, are directed to using a template 2 after the graft 22 has been positioned in the intervertebral space 18 and before the implantation of the final plate 26.

Template

Figure 2:
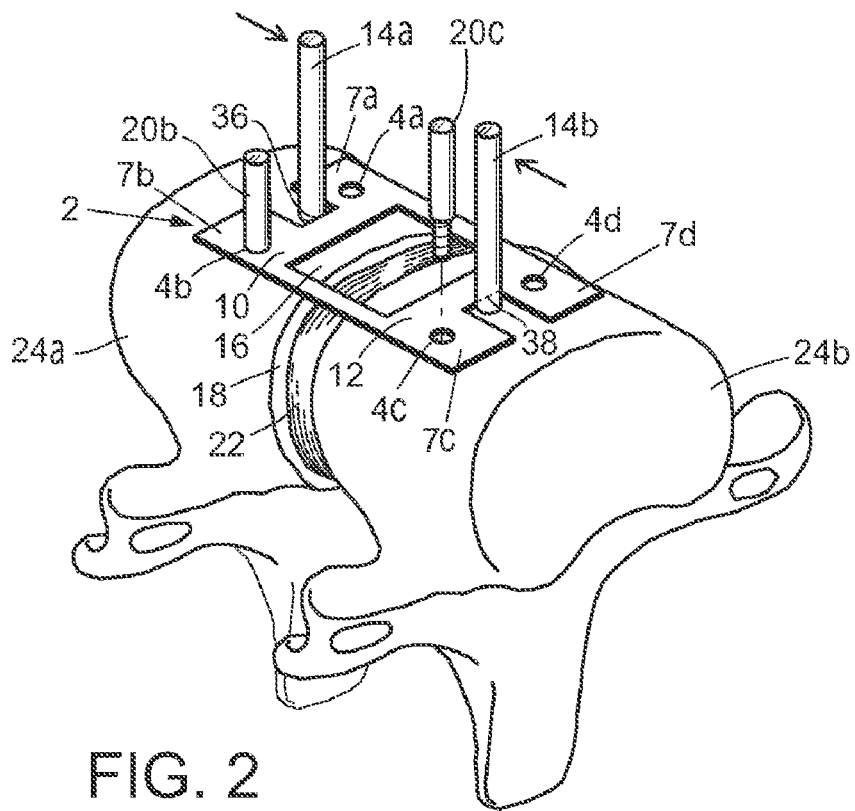
FIG. 2 is a perspective view of holding pins being inserted though a preferred template positioned on adjacent vertebral bodies.
Figure 3:
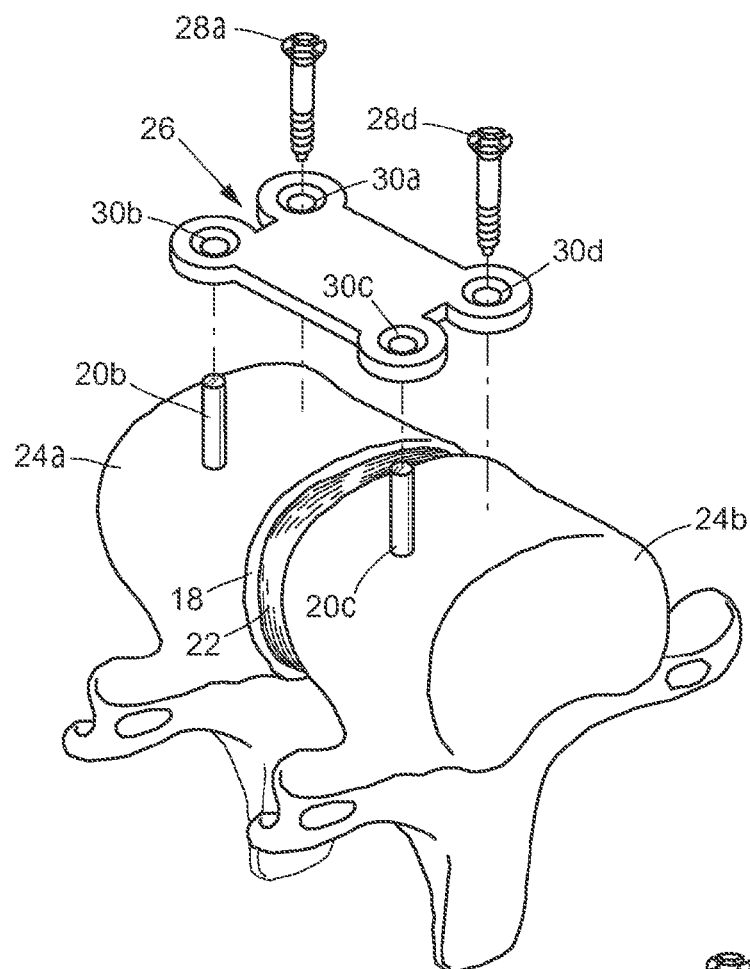
FIG. 3 is an exploded view of a preferred final plate being aligned to adjacent vertebral bodies through the use of holding pins.

FIG. 1 depicts a perspective view of a preferred template 2 being aligned over a superior vertebral body 24*a* and inferior vertebral body 24*b*. The term "template" as used herein generally relates to devices that are not permanent implants and have one or more windows configured to allow a surgeon to view an intervertebral space. Preferably templates include two or more apertures to allow holding pins or other markers to be placed into the surrounding vertebrae that guide or mark where the final plate will be positioned. While the template 2 depicted in FIGS. 1 and 2 is a preferred model and is predominately described herein, the described features and methods of this template 2 can expressly be used on other template configurations described herein, such as 2*a*, 2*b*, 2*c*, 2*d*.

FIGS. 1, 2, 7-9, depict templates 2, 2*a*, 2*b*, and 2*c* that are designed to be positioned on two vertebral bodies and are useful for corpectomies and single-level disectomies. Alternatively, and as shown in FIG. 10*c*, longer templates 2*d* having three or more sections individually configured to be placed on three or more different vertebrae 24*a*, 24*b* and 24*c* can be used for multi-level disectomies, for example According to preferred embodiments, a template 2 can include an upper section 10 configured to be positioned on the superior vertebral body 24*a* and a lower section 12 configured to be positioned on the inferior vertebral body 24*b*. According to advantageous embodiments, the template includes a window 16 configured to provide the surgeon with a view of the intervertebral area 18, and/or the interbody implant 22. Preferably the window 16 is located in the center of the template 2, or substantially so, or at other locations that allow the surgeon to view the intervertebral area 18, and/or the interbody implant 22.

A multi-level template 2*d* can include two or more windows, such as an upper window 16*a* and a lower window 16*b*, to view the two or more intervertebral spaces it covers when positioned on three or more vertebral bodies 24*a*, 24*b*, and 24*c*. More particularly the multiple windows can be separated by one or more template sections 44 configured to be positioned on a middle vertebral body 24*c*. Alternatively, a multilevel template can include one large window configured to view both intervertebral spaces, and lack the separating section.

Templates having a window 16 configured to view the interbody 18 and/or graft 22 is highly advantageous as it allows the surgeon to better ascertain the position of the final plate 26. Additionally, the window 16 lessens the chances of the surgeon accidentally placing a holding pin 20*b* and 20*c*, or final screw 28*a-d*, into the bone graft 22 which could dislodge it and push it into the spinal cord. According to preferred embodiments, the window 16 can be an open hole or a hole covered by a transparent material such as clear plastic or glass, for example.

According to more specific embodiments, the upper section 10 of the template 2 can be partially bisected by a vertical slot 6*a* configured to receive a first distractor pin 14*a* and that effectively divides the upper section 10 of the template 2 into a right corner area 7*a* and left corner area 7*b*. According to more specific embodiments, the vertical slot 6*a* begins in the middle of the upper perimeter of the template 2, or substantially so, and bisects downward towards the upper border of the template window 16 to an end point 36. Likewise, it is preferred that the lower section 12 of the template 2 is partially bisected by a second vertical slot 6*b*, configured to receive a second distractor pin 14*b*, and that effectively divides the lower section 12 of the template 2 into a right corner area 7*d* and a left corner area 7*c*. According to more specific embodiments, the vertical slot 6*b* begins in the middle of the lower perimeter of the template 2, or substantially so, and bisects upwards towards the lower border of the template window 16 to an end point 38.

According to advantageous embodiments where the slots 6*a* and 6*b* are located in the middle of the template 2, or substantially so, they are useful for centering the template 2 and the corresponding final plate 26 along the vertebral midline. The end points 36 and 38 of the slots 6*a* and 6*b* are useful in aligning the template 2 against the distractor pins 14*a* and 14*b*. Additionally, the end points 36 and 38 are helpful in preventing over-compression by the distractor pins which can damage the graft 22.

For a multi-level template 2*d* the upper slot 6*a* can bisect the top portion of the template into left and right corner areas 7*b* and 7*a* as it traverses downward towards the upper border of the upper window 16*a*. Likewise the lower slot 6*b* can bisect the lower portion of the template into left and right corner areas 7*c* and 7*d* as it traverses upwards towards the lower border of the lower window 16*b*. Alternatively the upper and lower slots can bisect towards a single large window that allows viewing of two or more intervertebral spaces.

Preferred templates described herein can be made of any suitable material including titanium, surgical steel, aluminum, or other metal, or hard plastic, for example.

It is preferred that the size and shape of each differently sized template 2 corresponds to a certain size and shape of final plate 26. Examples of current fusion plates used in the art, are those produced by EBI Biomet, Inc., Dupuy AcroMed, Inc., and Spinal Concepts, Inc, to name a few. Accordingly, it is preferred to provide templates 2 that align with different sizes and designs of these and other available plates.

It is highly preferable that the screw holes 30*a-d* of the final plate 26 align with the pin apertures 4*a-d* on the template 2 if the plate 26 were to be overlaid on top of the template 2. The alignment of the template 2 with the final plate 26 ensures that the holding pins 20*b* and 20*c* are correctly positioned into the vertebral bodies 24*a* and 24*b* and that they effectively guide the final plate's screw apertures 30*a-d* to their appropriate positions on the vertebral bodies 24*a* and 24*b* to receive the final screws 28*a-d*.

More specifically, the template 2 can include 1, 2, 3, 4, 5, 6 or more holding pin apertures that align with one or more, or all, screw apertures located on the final plate 26. Further embodiments can utilize 2, 3, 4, 5, 6, or more holding pins depending on the preference of the surgeon, the number of apertures on the template, and the configuration of the template. It is preferred that the templates provided herein include four apertures as most fusion plates have four apertures, and this allows the surgeon to determine where all of the final screws 28*a-d* will be secured into the patients vertebrae 24*a* and 24*b*. In more preferred embodiments, it is advantageous that the templates 2 provided herein include the same number of holding pin apertures as there are screw holes on the final plate 26.

The holding pin apertures 4*a-d*, are preferably located in the corner areas 7*a-d* or around the sides of the templates 2.

Likewise, the screw holes 30a-d are also preferably positioned in the corner areas or around the sides of the final plate 26.

As preferred embodiments only utilize two holding pins, it is also readily contemplated herein to utilize templates that have the same number of holding pins apertures as holding pins used. This number could be two, three, four, or more for example. For embodiments directed to templates having a number of holding pin apertures that is smaller than the number of screw apertures on the corresponding final plate, it is preferred that the screw apertures that do not correspond to a holding pin aperture are positioned correctly against the vertebrae 24a and 24b when the targeted screw holes are placed over the holding pins. For example, if a template only had two holding pin apertures 4b and 4c (4a and 4d are not present), it is preferred that when the aligned screw holes 30b and 30c of the final plate 26 are placed over the holding pins 4b and 4c, the remaining screw holes 30a and 30d are positioned in their proper place along the superior and inferior vertebral bodies 24a and 24b for the final screws 28a and 28d to properly secure the plate 26. For embodiments where only two holding pin apertures are used, it is preferred that they are positioned in vertically aligned corners or alternatively in horizontally or diagonally aligned positions.

According to alternative embodiments, the multi-level template 2d can include six or more holding pin apertures 4a-f that align with the six screw holes 30a-f on the multi-level plate 26a. Preferably, the separating section 44, can include pin holes 4f and 4e configured to receive their own holding pins. Further embodiments entail only 1 row of vertically aligned holding pin apertures, such as only 4b, 4f, 4c or 4a, 4e, and 4d. Alternatively, the multi-level template could have only two holding pin apertures that are vertically aligned, such as 4b and 4c or 4a and 4d.

Figure 7:
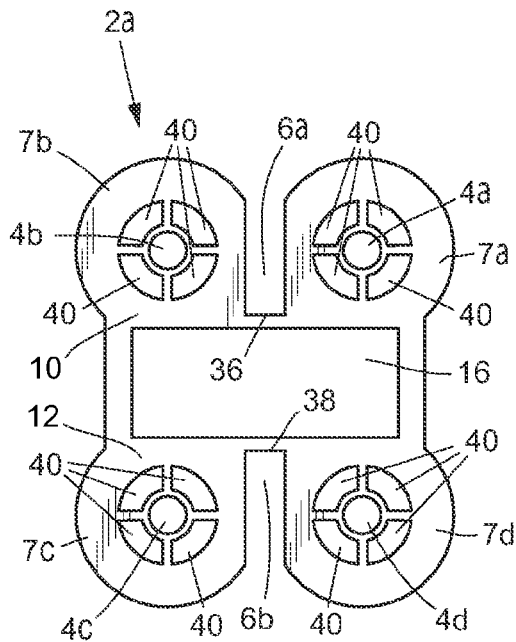
FIG. 7 is a planar view of an alternative template.
Figure 8:
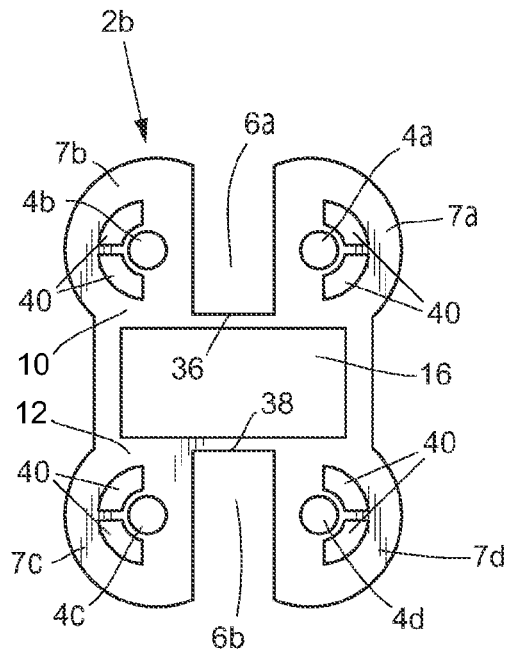
FIG. 8 is a planar view of a narrow alternative template

The corner areas of the template 2 and/or the final plate 26 can be any suitable geometrical shape, including right angles, circular, semi-circular, chamfered, filleted, or bull-nosed, or substantially so, for example. FIG. 7 depicts a template 2a having substantially circular corner areas, FIG. 8 depicts a template 2b having substantially semi-circular corner areas. Both of these templates 2a and 2b include one or more openings 40 surrounding the pin holes apertures 4a, b, c, and d to allow better viewing of the vertebrae area such as to improve proper placement of the holding pin 20b and 20c.

After the appropriate sized template 2 is determined, the surgeon can then select a corresponding final plate 26. If the surgeon already knows the size and shape of the final plate 26, it may be possible to utilize a single template 2 to determine the proper position of the final plate 26 on the targeted vertebrae 24a and 24b. However, as most surgeons will not immediately know the size of the final plate 26, he can individually test multiple sizes and/or shapes of templates 2 against the vertebrae 24a and 24b while the distractor is compressing the distractor pins 14a and 14b until the appropriate size and shape of the final plate 26 can be determined.

Figure 9:
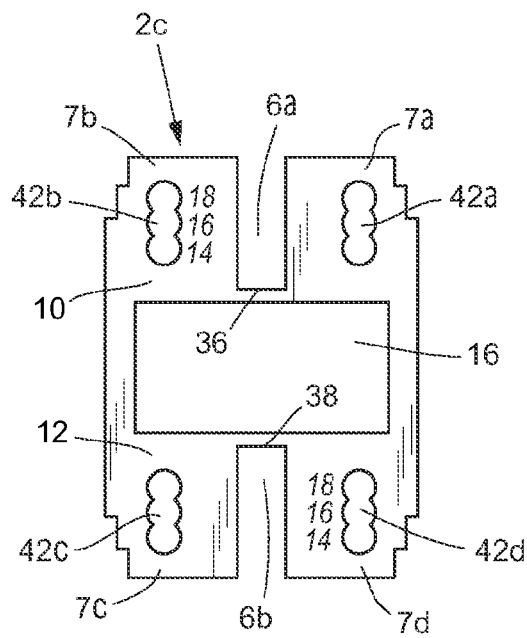
FIG. 9 is a planar view of a multi-size template.
Figure 10A:
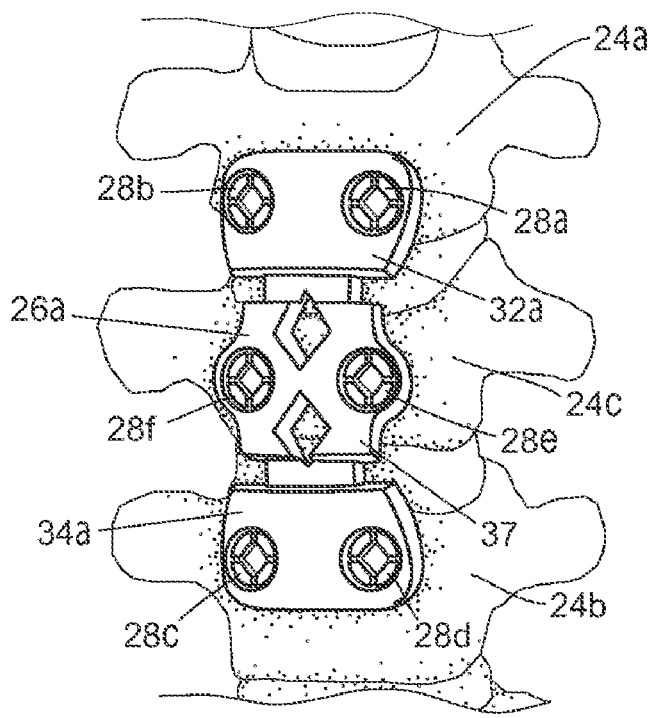
FIG. 10A is a view of a multi-level final plate secured to three vertebrae.
Figure 10B:
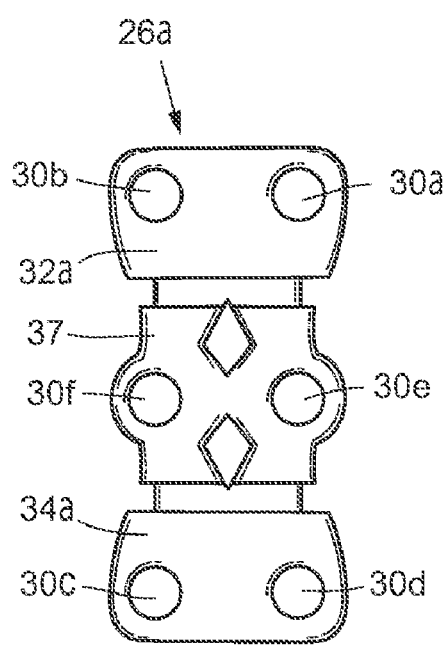
FIG. 10B is a view of a multi-level final plate.
Figure 10C:
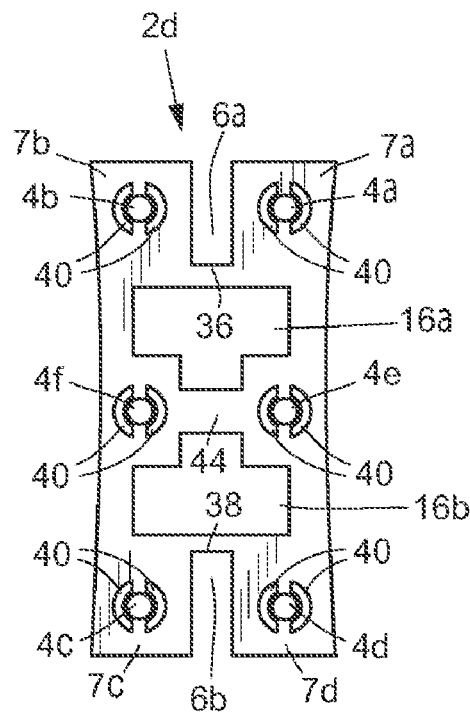
FIG. 10C is a view of a multi-level template.

According to alternative embodiments, instead of utilizing multiple different templates to ascertain the correct size of final plate, a surgeon could use a single multi-size template 2c such as provided in FIG. 9, for example. Multi-size templates 2c preferably include variable-size holding pin apertures 42a-d that individually include multiple positions for a holding pin to be placed. More specifically, the multiple positions within the variable-size holding pin apertures 42a-d correspond to different sizes of final plates and are preferably incrementally separated. More specifically, the variable-size holding pin apertures 42a-d can include two, three, four, five, or more positions to hold a holding pin. FIG. 9, as an example, depicts variable-size holding pin apertures 42a-d having three positions that corresponds with various sizes of final plates: 14, 16, 18 mm. After placing the multi-size template 2c against the vertebrae 24a and 24b and the intervertebral space 18, the surgeon could look at the position of variable-size apertures 42a-d and ascertain the proper size of the final plate 26 and place two or more holding pins into the corresponding position within two or more variable-size holding pin apertures 42a-d. A final plate having screw holes with variable-size positions is also readily contemplated to be used with the teachings herein.

Methods of Use

In preferred methods, after placing the graft 22 into the interbody space 18 the surgeon aligns the upper and lower slots 6a and 6b of the template onto the upper and lower distractor pins 14a and 14b respectively and positions the template 2 towards the superior and inferior vertebral bodies 24a and 24b. In highly advantageous embodiments, it is preferred that the surgeon uses a distractor and/or retractor engaged with the distractor pins 14a and 14b to mechanically compress the superior and inferior vertebral bodies 24a and 24b as the template 2 is positioned downward toward them. This mechanical compression is advantageous as it can apply greater pressure to the graft 22 than the natural compression of the vertebral bodies 24a and 24b by themselves. By increasing the pressure, the surgeon significantly increases the chances of a successful fusion.

Preferably while the template 2 is positioned against the compressed vertebral bodies 24a and 24b, the surgeon can place holding pins 20b and 20c in the apertures 4b and 4c. Preferably, the holding pins 20b and 20c are made of metal, such as titanium or stainless steel, and are screwed into the vertebrae, although other suitable methods can be used. More specifically, it is preferred that the holding pins 20b and 20c include a threaded portion configured to be secured within the vertebra and an exposed portion configured to pass through its designated aperture 4b and 4c. While different numbers of apertures and holding pins can be used with the systems and methods provided herein, it is preferred that only two holding pins are utilized. More specifically it is preferred that the two holding pins are positioned on the same side of each other, individually in apertures that are vertically aligned from one another. For example, as depicted in FIG. 2, holding pins 20b and 20c are respectively placed in the aperture 4b located in the upper left corner 7b and the aperture 4c located in the lower left corner area 7c. In alternative preferred embodiments, holding pins can individually be place in the upper right aperture 4a and the bottom right aperture 4d (not shown).

In further non-preferred embodiments, the two holding pins can be placed in apertures that are positioned diagonally from one another. For example, holding pins can individually be placed in the upper left corner 7b and the lower right corner 7d of the template, or alternatively in the upper right corner 7a and the lower left corner 7c of the template 2. In still further non-preferred embodiments, the 2 holding pins can be placed in apertures that are positioned horizontally from one another, for example the upper left and right 7b 7a or lower left and right corner areas 7c 7d. As will be explained below, this is especially not advantageous because the horizontally positioned holding pins will not allow for any vertical compression of the interbody graft 22 when the final plate 26 is implanted.

According to preferred embodiments, the holding pins 20b and 20c are not designed to permanently secure the template 2 to the vertebral bodies 24a and 24b, but rather serve as guides for the final plate 26 and to allow for vertical compression of the intervertebral space 18. According to preferred embodiments, the apertures of the template 4b and 4c and the holding pins 20b and 20c are configured such that the surgeon can readily remove the template 2 from the vertebral bodies 24a and 24b without having to remove the holding pins 20b and 20c. More specifically, the apertures 4b and 4c advantageously, can have a larger diameter than the holding pins 20b and 20c. In more specific embodiments, it is preferred that the holding pins 20b and 20c are positioned in the middle of the apertures 4b and 4c on the template, or substantially so. Additionally, it is preferred that the template 2 can be removed while the distractor pins 14a and 14b are still inserted into their respective vertebrae 24a and 24b, regardless of whether they are engaged or unengaged with a distractor.

While preferred embodiments provided herein are directed to systems and methods using holding pins 20b and 20c, it is further contemplated to use other non-preferred means for marking the position of the final plate 26. Any suitable visual markers can be utilized with the templates 2 provided herein to guide the position of the final plate, including but not limited to etchings, dyes, pen or pencil markings, or ink, for example. The above markers can be made in one or more holding pin apertures in the template or can be made to indicate the perimeter of the final plate, for example. Non-pin embodiments are not preferred as they do not allow for vertical compression of the intervertebral space 18.

After the holding pins 20b and 20c are placed into the vertebrae, the template 2 and distractor pins 14a and 14b can be removed. After the distractor tool is disengaged from the distractor pins 14a and 14b and/or the distractor pins 14a and 14b are removed from the vertebral bodies 24a and 24b, the intervertebral space will return to its natural uncompressed state. Alternatively distractor pins can be left in for enhanced compression and the final plate can be placed according to the methods of U.S. Pat. No. 6,648,891. Preferably, the holding pins 20b and 20c are left in the vertebral bodies 24a and 24b as guides for the final plate 26 and to allow for compression of the intervertebral space 18 as the final plate 26 is secured. More specifically, it is preferred that apertures 30b and 30c of the final plate 26 are configured such that when they slide down the holding pins 20b and 20c towards the vertebral bodies 24a and 24b, pressure will force the exposed (top) portion of the holding pins 20b and 20c to converge towards each other (FIGS. 4 and 5), and the bottom portion of the holding pins 20b and 20c embedded in the vertebral bodies 24a and 24b to diverge from each other (FIG. 5). This manipulation of the holding pins 20b and 20c causes vertical compression on the intervertebral space 18 and preferably the interbody graft 22. Advantageously, this vertical compression is equal to, or similar to the original compression of the vertebral bodies 24a and 24b generated by the distractor and the distractor pins 14a and 14b. Alternatively it is lesser compression than obtained by the distractor.

Figure 4:
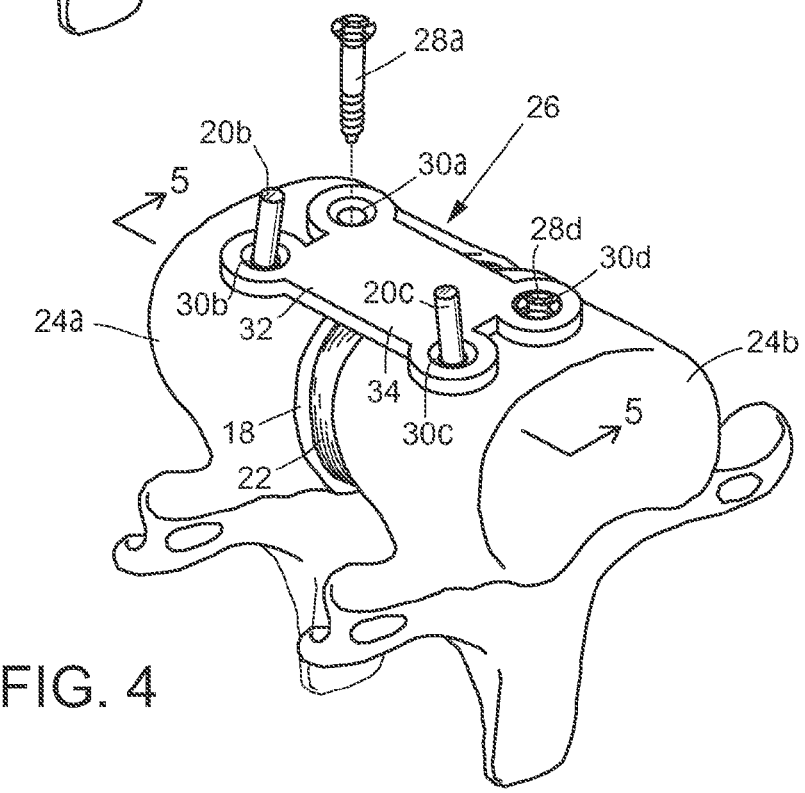
FIG. 4 is a perspective view of a preferred final plate in the process of being secured to adjacent vertebral bodies.
Figure 5:
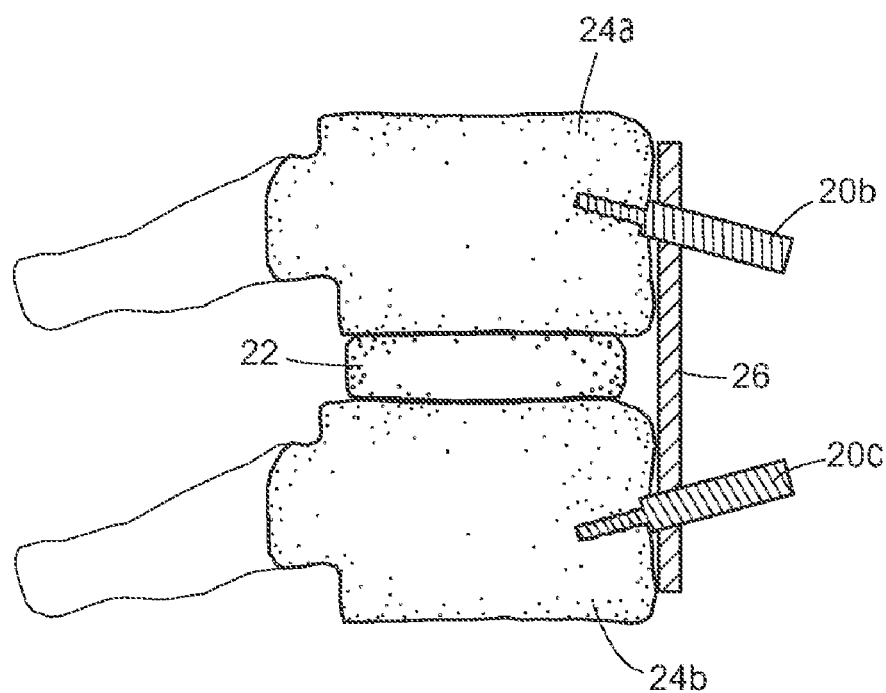
FIG. 5 is a side view of FIG. 4, showing a preferred final plate in the process of being secured to adjacent vertebral bodies
Figure 6:
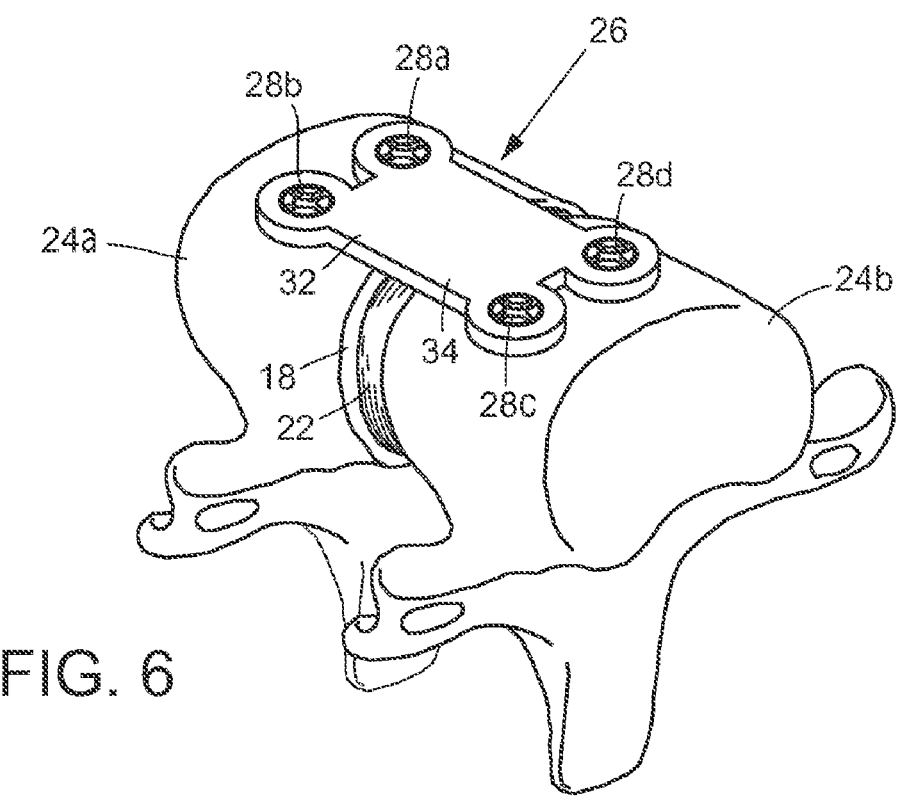
FIG. 6 is a perspective view showing a preferred final plate secured to adjacent vertebral bodies.

Once the plate 26 is pressed against the vertebral bodies 24a and 24b and the intervertebral space 18 is compressed by the holding pins 20b and 20c, the final screws 28a and 28d can be secured through the open holes 30a and 30d as shown in FIG. 4. After the screws 28a and 28d are secured to the vertebral bodies 24a and 24b the compression of the intervertebral space 18 is maintained and the holding pins 20b and 20c can be removed without allowing expansion of the intervertebral space 18. Final screws can then replace the holding pins 20b and 20c through the holes 30b and 30c to permanently affix the final plate 26 to the vertebral bodies 24a and 24b.

The invention may be embodied in other specific forms besides and beyond those described herein. The foregoing embodiments are therefore to be considered in all respects illustrative rather than limiting, and the scope of the invention is defined and limited only by the appended claims and their equivalents, rather than by the foregoing description.

What is claimed is:

1. A method of using a template to select a fusion plate for implanting onto a superior and inferior vertebral body having a graft implanted between a first intervertebral space comprising:
   (a) inserting a first distractor pin into the superior vertebral body and a second distractor pin into the inferior vertebrae;
   (b) engaging said distractor pins with a distractor;
   (c) compressing the intervertebral space and graft with the distractor;
   (d) providing a template comprising
      (i) a top section configured to be positioned on the superior vertebral body and comprising a first vertical slot adapted to receive the first distractor pin and that divides the top section into first and second upper corner areas, wherein at least one of the upper corner areas comprise a first holding pin aperture;
      (ii) a bottom section configured to be positioned on the inferior vertebral body and comprising a second vertical slot adapted to receive the second distractor pin and that divides the bottom section into first and second lower corner areas, wherein at least one of the lower corner areas comprises a second holding pin aperture; and
      (iii) a first window positioned between the top and bottom sections and adapted to be positioned over the first intervertebral space;
   (e) placing the template on the compressed superior and inferior vertebrae such that the first vertical slot receives the first distractor pin, the second vertical slot receives the second distractor pin, and the first window is positioned over the first intervertebral space; and
   (f) selecting a final fusion plate for implantation onto the superior and inferior vertebral bodies that comprises first and second screw holes aligned with the first and second holding pin apertures on the template.

2. The method of claim 1, wherein the first and second holding pin apertures on the template are vertically aligned with another.

3. The method of claim 1, wherein the four corner areas of the template each include a holding pin aperture.

4. The method of claim 1, wherein the first and second holding pin apertures are variable-size apertures that individually include multiple positions for a holding pin to be placed.

5. The method of claim 1, further comprising a middle section configured to be positioned against a middle vertebral body in between the superior and inferior vertebral bodies.

6. The method of claim 5, wherein the first window is positioned between the top and middle sections of the template and is configured to be positioned over the first intervertebral space between the superior and middle vertebral bodies and wherein the template further comprises a second window positioned between the bottom and middle sections of the template and is configured to be positioned over a second intervertebral space between the inferior and middle vertebral bodies.

7. A method of using a template for implanting a fusion plate onto a superior and inferior vertebral body having a graft implanted between a first intervertebral space comprising:

(a) inserting a first distractor pin into the superior vertebral body and a second distractor pin into the inferior vertebrae;

(b) engaging said distractor pins with a distractor;

(c) compressing the intervertebral space and graft with the distractor;

(d) providing a template comprising (i) a top section configured to be positioned on the superior vertebral body and comprising a first vertical slot adapted to receive the first distractor pin and that divides the top section into first and second upper corner areas, wherein at least one of the upper corner areas comprise a first holding pin aperture;

(ii) a bottom section configured to be positioned on the inferior vertebral body and comprising a second vertical slot adapted to receive the second distractor pin and that divides the bottom section into first and second lower corner areas, wherein at least one of the lower corner areas comprises a second holding pin aperture; and (iii) a first window positioned between the top and bottom sections and adapted to be positioned over the first intervertebral space;

(e) placing the template on the compressed superior and inferior vertebrae such that the first vertical slot receives the first distractor pin, the second vertical slot receives the second distractor pin, and the first window is positioned over the first intervertebral space;

(f) selecting a final fusion plate for implantation onto the superior and inferior vertebral bodies that comprises first and second screw holes aligned with the first and second holding pin apertures on the template;

(g) placing a first holding pin into the superior vertebral body through the first holding pin aperture;

(h) placing a second holding pin into the inferior vertebral body through the second holding pin aperture;

(i) removing the template from the superior and inferior vertebral bodies;

(j) removing distractor pins from the superior and inferior vertebral bodies;

(k) placing the fusion plate onto the superior and inferior vertebral bodies such that the first and second holding pins pass through the first and second aligned screw holes on the fusion plate and compress the first intervertebral space; and (l) securing said fusion plate to the superior and inferior vertebral bodies.

8. The method of claim 7, wherein the first and second holding pin apertures on the template are vertically aligned with another.

9. The method of claim 7, wherein the first and second holding pin apertures are variable-size apertures that individually include multiple positions for a holding pin to be placed.

10. The method of claim 7, further comprising a middle section configured to be positioned against a middle vertebral body in between the superior and inferior vertebral bodies.

11. The method of claim 10, wherein the first window is positioned between the top and middle sections of the template and is configured to be positioned over the first intervertebral space between the superior and middle vertebral bodies and wherein the template further comprises a second window positioned between the bottom and middle sections of the template and is configured to be positioned over a second intervertebral space between the inferior and middle vertebral bodies.

\* \* \* \* \*